(12) United States Patent
Fearnot et al.

(10) Patent No.: US 9,814,444 B2
(45) Date of Patent: Nov. 14, 2017

(54) FEEDBACK/REGISTRATION MECHANISM FOR ULTRASOUND DEVICES

(71) Applicant: Muffin Incorporated, West Lafayette, IN (US)

(72) Inventors: Neal E. Fearnot, West Lafayette, IN (US); Peter S. McKinnis, West Lafayette, IN (US); Sarah Robbins, Lafayette, IN (US); Yun Zhou, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 644 days.

(21) Appl. No.: 14/051,846

(22) Filed: Oct. 11, 2013

(65) Prior Publication Data

US 2014/0107490 A1   Apr. 17, 2014

Related U.S. Application Data

(60) Provisional application No. 61/713,142, filed on Oct. 12, 2012.

(51) Int. Cl.
*A61B 8/00* (2006.01)
*A61B 8/12* (2006.01)
(Continued)

(52) U.S. Cl.
CPC .............. *A61B 8/4483* (2013.01); *A61B 8/12* (2013.01); *A61B 8/445* (2013.01); *A61B 8/4461* (2013.01);
(Continued)

(58) Field of Classification Search
CPC .. G10K 11/004; G10K 11/357; A61B 8/4461; A61B 8/12; A61B 8/445;
(Continued)

(56) References Cited

U.S. PATENT DOCUMENTS 4,421,118 A   12/1983 Dow et al.
4,720,266 A   1/1988 Leonard et al.
(Continued)

FOREIGN PATENT DOCUMENTS

JP   2004/129697       4/2004
JP   2007 000293 A     1/2007
WO   WO 2012/061643 A1 5/2012

OTHER PUBLICATIONS

International Search Report and Written Opinion issued in PCT/US2013/064570, dated Jan. 24, 2014.
(Continued)

*Primary Examiner* — Long V Le
*Assistant Examiner* — Colin T Sakamoto
(74) *Attorney, Agent, or Firm* — Woodard, Emhardt, Moriarty, McNett & Henry LLP

(57) ABSTRACT

Among other things, there is disclosed structure and methods for registering images obtained through internal (e.g. intravascular) ultrasound devices. Embodiments of a device with a rotating ultrasound beam is provided, with a wall of the device being anisotropic in ultrasound passage. As examples, a cable opaque to ultrasound is attached along the wall of the device, so that the ultrasound beam at the location of the cable is blocked, reflected or scattered. As another example, a thin film of metallic material is placed on or in the wall to allow a portion of the beam to be blocked or attenuated. The imaging system recognizes the changes to the signals made by the anisotropic wall, and registers successive images according to those changes.

13 Claims, 4 Drawing Sheets

(51) Int. Cl.
　　*G01S 15/89*　　(2006.01)
　　*G01S 7/52*　　(2006.01)
　　*G10K 11/35*　　(2006.01)
　　*G10K 11/00*　　(2006.01)
　　*A61B 90/00*　　(2016.01)

(52) U.S. Cl.
　　CPC ............ *A61B 8/4494* (2013.01); *A61B 8/461* (2013.01); *A61B 8/54* (2013.01); *G01S 7/5205* (2013.01); *G01S 15/8943* (2013.01); *G10K 11/004* (2013.01); *G10K 11/357* (2013.01); *A61B 8/4245* (2013.01); *A61B 90/39* (2016.02); *A61B 2090/3925* (2016.02)

(58) Field of Classification Search
　　CPC ....... A61B 8/54; A61B 8/4494; A61B 8/4483; A61B 8/461; G01S 15/8943; G01S 7/5205
　　See application file for complete search history.

(56) References Cited

U.S. PATENT DOCUMENTS

| | | | |
|---|---|---|---|
| 4,785,816 A | 11/1988 | Dow et al. | |
| 5,240,003 A * | 8/1993 | Lancee | A61B 8/12 310/162 |
| 5,373,845 A | 12/1994 | Gardineer et al. | |
| 5,377,685 A | 1/1995 | Kazi et al. | |
| 5,485,845 A * | 1/1996 | Verdonk | A61B 8/12 600/463 |
| 5,701,901 A | 12/1997 | Lum et al. | |
| 5,951,480 A | 9/1999 | White et al. | |
| 6,162,178 A | 12/2000 | Garcia et al. | |
| 6,241,744 B1 | 6/2001 | Imran et al. | |
| 6,371,915 B1 | 4/2002 | Koger et al. | |
| 6,684,094 B1 | 1/2004 | Lehr et al. | |
| 8,206,307 B2 | 6/2012 | Barnard et al. | |
| 2002/0082503 A1 | 6/2002 | Chandrasekaran et al. | |
| 2002/0087083 A1 | 7/2002 | Nix et al. | |
| 2002/0143252 A1 | 10/2002 | Dunne et al. | |
| 2006/0030797 A1 | 2/2006 | Zhou et al. | |
| 2006/0173348 A1 | 8/2006 | Wilser et al. | |
| 2007/0038114 A1 | 2/2007 | Couvillon, Jr. | |
| 2007/0149917 A1 | 6/2007 | Bennett et al. | |
| 2008/0097403 A1 | 4/2008 | Donaldson et al. | |
| 2008/0177138 A1 | 7/2008 | Courtney et al. | |
| 2008/0221506 A1 | 9/2008 | Rodriguez et al. | |
| 2009/0306518 A1 | 12/2009 | Kurse et al. | |
| 2010/0036258 A1 | 2/2010 | Dietz et al. | |
| 2010/0160788 A1 | 6/2010 | Davies et al. | |
| 2010/0234736 A1 | 9/2010 | Corl | |
| 2010/0249602 A1 | 9/2010 | Buckley et al. | |
| 2010/0249604 A1 | 9/2010 | Hastings et al. | |
| 2011/0021924 A1 | 1/2011 | Sethuraman et al. | |
| 2011/0071401 A1 | 3/2011 | Hastings et al. | |
| 2011/0196286 A1 | 8/2011 | Robertson et al. | |
| 2011/0263986 A1 | 10/2011 | Park et al. | |
| 2011/0301508 A1 | 12/2011 | Sethuraman et al. | |
| 2012/0172698 A1 | 7/2012 | Teo et al. | |

OTHER PUBLICATIONS

International Search Report and Written Opinion issued in PCT/US2013/064579, dated Jan. 23, 2014.
International Search Report and Written Opinion issued in PCT/US2013/064606, dated Jan. 8, 2014.
International Search Report and Written Opinion issued in PCT/US2013/064611, dated Jan. 28, 2014.
International Search Report and Written Opinion issued in PCT/US2013/064618, dated Jan. 24, 2014.
Office action, Chinese appln. 201380064735.4, dated Jul. 22, 2016, 15 pgs.

* cited by examiner

FEEDBACK/REGISTRATION MECHANISM FOR ULTRASOUND DEVICES

CROSS-REFERENCE TO RELATED APPLICATIONS

The present application claims the benefit of U.S. Provisional Application Ser. No. 61/713,142, filed on Oct. 12, 2012, and incorporates by reference the same herein in its entirety.

The present disclosure concerns ultrasound devices for use internally and resolution of problems existing in rotating mechanical scan ultrasound devices.

BACKGROUND

A number of ultrasound imaging devices and systems have been proposed, and in many the problem exists of ensuring that each of the frames of an image acquired by the ultrasound device are properly registered with each other. Without such registration, there is the possibility that variance in mechanical movement of an ultrasound transducer, or inadvertent or purposeful movement of the device, will be unaccounted for in the image observed by the physician, resulting in undesirable changes in orientation or content of images.

For example, there are proposed devices in which an ultrasound transducer is turned (e.g. by a motor) around a longitudinal axis of the device (e.g. U.S. Pat. No. 8,214,010 to Courtney et al.). However, in some cases over time the positional error (i.e. the difference between the desired or intended position of the motor's rotor and its actual position relative to bodily tissue) can quickly grow to unacceptable levels. Even small velocity errors in the motor, when accumulated, can make an image appear to rotate on an ultrasound viewing screen or console, giving the impression that the imaging device is being physically rotated within the body even though it is stationary.

To address such a disconcerting or confusing and false effect, a rotary feedback mechanism may be used to precisely measure angular position so that each image frame acquired through ultrasound imaging is registered (i.e. oriented appropriately) with respect to previous frames. While a variety of rotary encoders are commercially available, such as hall effect sensors, incremental quadrature encoders, absolute gray encoders and potentiometers, such off-the-shelf devices are too bulky and complex to fit into an intravascular or other low profile device. There is thus a need for a registering device or system that is reduced in bulk and simpler, in order to maintain or reduce overall size and usability of IVUS devices.

SUMMARY

Among other things, there is disclosed an internal ultrasound device with a rotary feedback system for registering successive images with one another. In particular embodiments, an ultrasound device (e.g. an intravascular ultrasound or IVUS device) with a rotary feedback system includes a transducer for emitting an ultrasound beam, the beam being rotatable around a longitudinal axis, and wherein the transducer is adapted to emit the beam and to receive reflected ultrasound and transform the reflected ultrasound into electronic signals, and an ultrasound control and/or analytical (e.g. imaging) system electronically connected to the transducer for receiving the electronic signals from the transducer and for creating images from the electronic signals. A wall surrounding the transducer has an ultrasound attenuation that is different between two or more sections of the wall. The wall sections thus attenuate (e.g. reflects, refracts and/or absorbs) the beam to different degrees, resulting in electronic signals differing in at least one characteristic (e.g. amplitude) that is distinguishable by the control system. The system is adapted to monitor the electronic signals for one or more distinguishable characteristics in the electronic signals and to correlate them to an angular position, e.g. in a succession of images.

In particular embodiments, an internal ultrasound device with a feedback system includes a transducer for emitting and/or receiving an ultrasound beam, the beam adapted to rotate around at least a portion of the device, wherein the transducer is adapted to send electronic signals, the electronic signals representing one or more qualities of ultrasound energy along a path of the beam. A wall surrounds the transducer, the wall having a first portion affecting the ultrasound beam in a first fashion (e.g. attenuating the ultrasound beam to a first degree) and a second portion affecting the ultrasound beam in a second fashion (e.g. attenuating the ultrasound beam to a second degree which may be different from the first degree), so that the ultrasound beam as it rotates at least periodically travels along a path that intersects the first wall portion (e.g. is along a line that includes or a path between the first portion and the transducer), and as it rotates the beam at least periodically travels along a path that intersects the second wall portion (e.g. a line that includes or a path between the second portion and the transducer). An ultrasound control system is electronically connected to the transducer for receiving and assessing the electronic signals from the transducer. A first electronic signal sent by the transducer representing one or more qualities of ultrasound along a path that intersects the first wall portion (e.g. between the transducer and the first portion) has at least one characteristic different from a second electronic signal sent by the transducer representing one or more qualities of ultrasound along a path that intersects the second wall portion (e.g. between the transducer and the second portion). The ultrasound control system is adapted to detect the at least one characteristic and to register a plurality of the electronic signals with each other by reference to the at least one characteristic.

Specific examples include those in which the first and second portions of the wall are located so that the ultrasound beam must travel further before interacting with the first portion than the ultrasound beam must travel before interacting with the second portion, so that the first electronic signal is delayed relative to the second electronic signal, and those in which the first portion of the wall reflects at least a portion of the ultrasound beam so that the first electronic signal has an amplitude greater than the amplitude of the second electronic signal. The second portion of the wall can include a material with a relative low acoustic impedance (e.g. low mismatch with a surrounding or adjacent environment), and the first portion of the wall includes a linear member with a relative high acoustic impedance (e.g. high mismatch with a surrounding or adjacent environment). In the example of use in an environment within a blood vessel or adjacent tissues, the second portion of the wall can include a material with acoustic impedance close to that of water, and the first portion of the wall (e.g. a linear member) is of or includes a material with acoustic impedance markedly higher than water. Such a linear member may be an electronic conductor, e.g. one connected to the transducer. Conductors can include a coaxial cable and/or a strip of metallic material. A linear member may be placed substantially parallel to an axis of rotation of the ultrasound beam. In some embodiments, the first portion of the wall includes a film of metallic material, and the second portion of the wall does not include the film of metallic material, so that the ultrasound attenuation of the first portion of the wall is different from the ultrasound attenuation of the second portion of the wall. A particular example is one in which there are two of the first portions and two of the second portions, the second portions being positioned at diametrically opposed locations. The two second portions may separate the two first portions into first and second electrically conductive parts, each of which is electrically connected to the transducer, so that the first electrically conductive part conducts signals to and/or from the transducer and the second electrically conductive portion is a ground. Suitable metallic materials include at least one of gold, platinum, rhodium, silver, copper and aluminum, and suitable thicknesses of the film or layer include approximately 1 nm to 20 µm.

Embodiments of internal ultrasound devices are also disclosed that include a transducer for emitting and receiving an ultrasound beam, the beam adapted to rotate around at least a portion of the device, wherein the transducer is adapted to send electronic signals, the electronic signals representing one or more qualities of ultrasound energy along a path of the beam, and a wall surrounding the transducer, the wall having an inner surface generally facing the transducer and an outer surface generally facing away from the transducer. The inner surface includes a first film of metallic material forming a first conductor, the first conductor being electronically connected to the transducer, and wherein the outer surface includes a second film of metallic material forming a second conductor, the second conductor being electronically connected to the transducer and electronically insulated from the first conductor. Particular examples have at least a portion of each of the first film and second film overlapping each other with the wall between them. Other embodiments may have first and second films or coatings on the same surface that do not overlap, as by sectioning the inner (or outer) wall or circumference and placing two coatings electrically insulated from each other on separated halves or other sections of the inner (or outer) circumference, thus having the coatings on the same surface but electrically isolated from one another. The first film can extend around the entirety of the inner surface's internal perimeter, and/or the second film can extend around the entirety of the outer surface's external perimeter. Specific embodiments use the first conductor as a signal conductor and/or the second conductor as a ground. The wall defines a window through which the ultrasound beam passes, and at least one of the first and second conductors may be at least partially within the window, and in such cases the portion of the at least one of the first and second conductors within the window permit ultrasound imaging through them.

A number of arrangements for turning the ultrasound beam with respect to the wall may be used. For example, the transducer may be directly or indirectly connected to a motor so that the transducer is rotatable in at least a 360 degree arc to turn the beam. As another example, the device may include a mirror that turns in at least a 360 degree path to reflect the beam from the transducer and the reflected ultrasound to the transducer.

As further discussed below, embodiments of encoders that can be used in an ultrasound transducer assembly (e.g. for use in intravascular ultrasound or IVUS) are disclosed. The ultrasound attenuation characteristic(s) of the housing or a wall portion for a transducer assembly are varied between or among at least two portions. As the ultrasound beam is rotated, the beam will pass through regions with different or varying levels of acoustic attenuation. Signals (e.g. RF signals) received from the transducer (as a result of an ultrasound signal) are monitored for changes in amplitude or other characteristics which reflects the acoustic attenuation difference(s) in the wall, and these signals (and the images or data created or derived from them) are correlated as to angular position of the beam.

DETAILED DESCRIPTION OF THE ILLUSTRATED EMBODIMENTS

Figure 1:
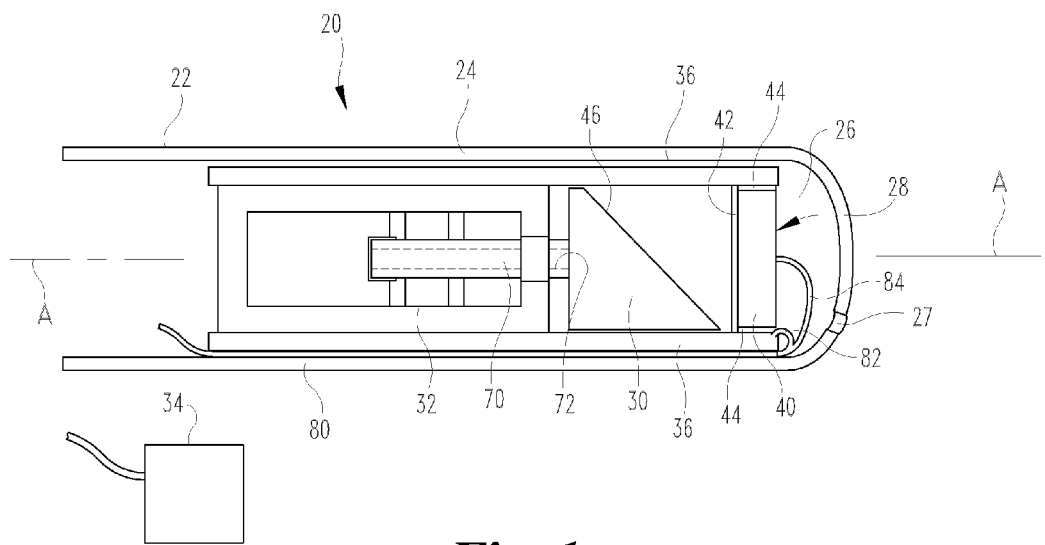
FIG. 1 is a schematic representation of an embodiment of an internal ultrasound device as further disclosed herein.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated embodiments, and such further applications of the principles of the disclosure as illustrated therein being contemplated as would normally occur to one skilled in the art to which the disclosure relates.

Referring now generally to the drawings, there are shown embodiments of a device 20 for providing ultrasound inside the body. Such devices may be diagnostic or therapeutic (including interventional) in application, and include devices inserted percutaneously, subcutaneously or endoluminally into the patient. Among other things, this disclosure provides an ultrasound encoder inside of an acoustic window (e.g. a portion of a catheter wall) without sacrificing image quality. Two techniques are suggested, one of which focuses on reflection, by adding one or more markers to a catheter wall that strongly reflect ultrasound. The marker may be small so that the reflected ultrasound energy is small and overall image quality is not affected. Another technique focuses on attenuation, by varying the attenuation or acoustic impedance of discrete areas or portions of a catheter wall so that the amplitude of an electrical (e.g. RF) signal produced by a transducer will be dependent on the angular position, i.e., the portion of the wall through which an ultrasound beam and its echoes pass. The shape of areas with different acoustic attenuation can be arbitrary, small or large, but in preferred embodiments are larger than beam width. Examples of such devices include embodiments designed for intravascular ultrasound (IVUS) imaging or treatment of deep vein thrombosis (DVT).

In the embodiment shown schematically in FIG. 1, device 20 is a flexible elongated member 22 (e.g. a catheter or other tubular member) having a wall 24 defining an internal chamber 26, with catheter 22 being sized and configured for insertion into and/or travel along the vascular system. Within chamber 26 is a transducer 28, which in this embodiment is for emitting an ultrasound beam and for receiving reflected ultrasound and sending electronic signals representing the reflected ultrasound. The illustrated embodiment includes an ultrasound reflective mirror 30, which is mounted to a rotary motor 32. It will be understood that transducer 28 could be connected (directly or indirectly) to motor 32 instead of mirror 30. An imaging system 34 is electronically connected to transducer 28, for displaying ultrasound images. Other features may be included in device 22, such as a two-axis gimbal mount or other pivoting mechanism for transducer 28 or mirror 30, to provide a wider or variable ultrasound field, and/or a linear motor with a shaft for forcing the mount and/or the transducer 28 to pivot. Examples are shown in the application filed on Oct. 12, 2012, entitled "Devices and Methods for Three-Dimensional Internal Ultrasound Usage" (Application Ser. No. 61/713,172), which is incorporated herein in its entirety.

Catheter 22 in the illustrated embodiment is an elongated device of plastic or other sturdy flexible material that presents a barrier to the passage of ultrasound signals small enough (i.e. the difference in acoustic impedance at the boundary of the material and the substances adjacent it) that ultrasound images may be reasonably acquired through the barrier. Wall 24 is a part of catheter 22 in this embodiment and thus is of the same ultrasound-transparent material. It surrounds at least part of chamber 26, which is at the distal end of device 20 in the illustrated embodiment, and extends proximally. The proximal end of wall 24 and/or catheter 22 may extend outside of the patient during use, and may end in a handle or other operating portion, such as imaging system 34 or a connection imaging system 34. Particular embodiments of catheter 22 or at least chamber 26 are cylindrical, and are sized for insertion into and passage through blood vessels, such as insertion into the femoral artery and passage through it toward the heart. At least a portion of wall 24 defines an ultrasound field or window 36 through which an ultrasound beam from transducer 28 exits, and through which reflected ultrasound travels to return to transducer 28.

Wall 24 may have a port 27 or other feature to allow injection of fluid into chamber 26. To address ultrasound reflectivity at the boundary between chamber 26 and blood or other body fluid in which device 20 is placed, a fluid F is placed in chamber 26 that presents ultrasound-carrying characteristics that are similar to the fluid outside of chamber 26. In particular embodiments, fluid F is a saline solution, so that the ultrasound characteristics within chamber 26 (saline) are similar to those outside chamber 26 (blood in a blood vessel). Port 27 allows a user to inject fluid F into chamber 26 just prior to use of device 20. Port P can then self-seal, so that little or no fluid F escapes from chamber 26. One or more seals may be placed in device 20 to separate fluid F in chamber 26 from motor 32.

Transducer 28 is indicated schematically in the drawings. The term "transducer" should be understood to include an assembly of two or more parts as well as a single piece. It will further be understood that "transducer" as used herein includes devices that transmit ultrasound (i.e. transform an electrical (RF) signal to ultrasound), receive ultrasound (i.e. transform ultrasound to an electrical (RF) signal), or both. If multiple transducers or pieces are provided, transmission of ultrasound may occur at one and reception at another. Transducer(s) as described herein may have one or more piezoelectric elements as respective transducers, and may operate in combination with other transducers within or outside the body.

Figure 2:
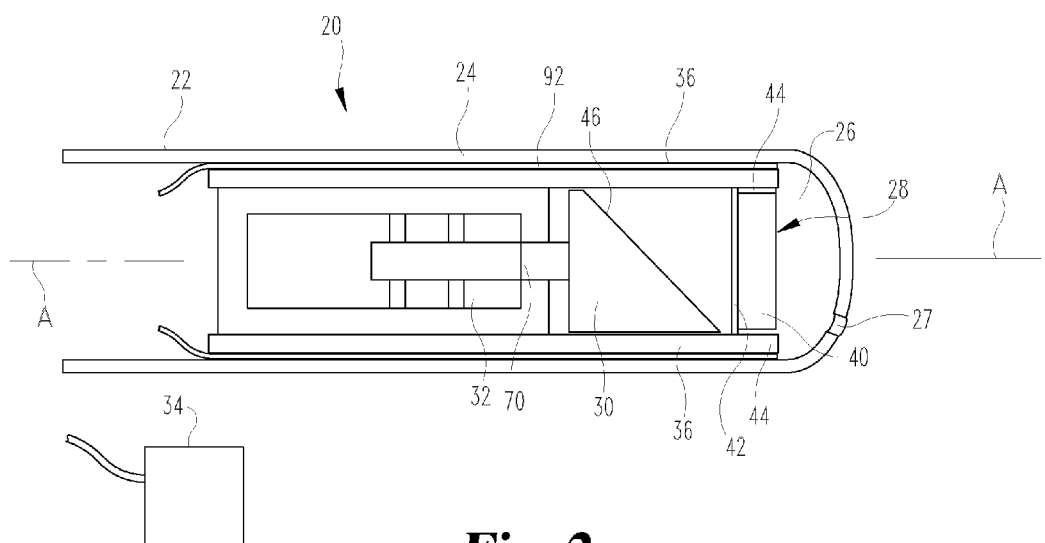
FIG. 2 is a schematic representation of an embodiment of an internal ultrasound device as further disclosed herein.
Figure 5:
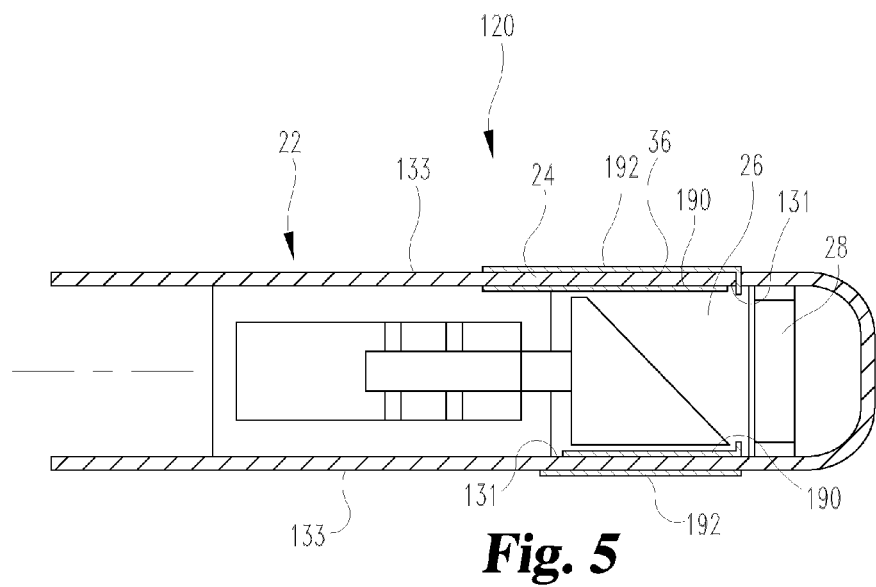
FIG. 5 is a schematic representation of an embodiment of an internal ultrasound device as further disclosed herein.

An exemplary transducer 28 includes a body or backing layer 40 with a piezoelectric element 42 attached to one side of body 40, and one or more clamping rings 44. An impedance matching layer (not shown) may also be attached to transducer element 42, e.g. opposite body 40 Transducer 28 is positioned at a far (i.e. further distant from the user) portion of chamber 26 and catheter 22 in the embodiments of FIGS. 1 and 2, with element 42 facing longitudinally and proximally as indicated in the drawings. Mirror 30 includes a surface 46 that reflects an ultrasound beam laterally (i.e. generally away from the longitudinal axis of catheter 22) through wall 24 within field 36. In the embodiment of FIG. 5, transducer 28 is attached to motor 32 so as to provide a generally lateral ultrasound beam direction. Body 40 may be substantially opaque to or reflective of ultrasound signals, so that such signals are effectively only projected laterally outward from piezoelectric element 42, e.g. to one side or in a limited angular range radially from transducer 28.

Rotary motor 32 includes a rotating shaft 70, for direct or indirect connection to mirror 30 (e.g. FIGS. 1 and 2) or transducer 28 (e.g. FIG. 5) in these embodiments. Rotary motor 32 is a microminiature motor suitable for containment within chamber 26 of catheter 22, preferably of a size of less than about 2.8 mm in diameter. Examples of such microminiature motors include piezoelectric or electromagnetic motors. For example, a particular embodiment of motor 32 is a two-phase, coreless, brushless DC electromagnetic motor, which has few components, small size and minimal complexity. Shaft 70 is hollow in the embodiment of FIG. 1 (i.e. defining a lumen 72 therethrough) and extends through the entirety of motor 32 (e.g. a dual shaft motor). Lumen 72 through shaft 70 permits passage of electronic conductors, (e.g. wires or cables), pulling or pushing mechanisms, and/or other features to pass through shaft 70, allowing transmission of electrical and/or mechanical force or energy through lumen 72 without affecting the turning of shaft 70.

Rotary motor 32 in the illustrated embodiments is configured to rotate shaft 70 continuously in a single rotational direction. In such embodiments, the ultrasound beam emitted by transducer 28 is rotated around the longitudinal axis of shaft 70 in that single rotational direction. It will be understood that rotary motor 32 may alternatively be configured to run in a reciprocating motion, with shaft 70 switching between rotation in a first rotary direction (e.g. for a predetermined time or number of turns) and rotation in a second, opposite, rotary direction (e.g. for a predetermined time or number of turns). An example of such a reciprocating device is described in Application Ser. No. 61/713,135, entitled "Reciprocating Internal Ultrasound Transducer Assembly" filed on Oct. 12, 2012, which is incorporated by reference herein in its entirety. As seen in the drawings, mirror 30 or transducer 28 can be fixedly mounted to shaft 70, which is along the overall longitudinal axis of device 20. As shaft or rotor 70 rotates, the ultrasound beam emitted by transducer 28 rotates at the same speed.

In the illustrated embodiments, the ultrasound beam or signals emitted and received by transducer 28 are used as a feedback mechanism to precisely assess or monitor the rotational position of rotary motor 32 (and the ultrasound beam rotated by it) relative to the rest of device 20, ensuring proper registration of images obtained through transducer 28. The illustrated embodiments include at least one feature that attenuates at least a portion of the ultrasound beam as it leaves catheter 22 at least one discrete location. For example, the embodiment shown in FIG. 1 includes a coaxial cable 80 fixed to the interior of wall 24 (i.e. within chamber 26) and passing through the ultrasound field 36 (i.e. the area through which the ultrasound beam from element 42 passes as the beam turns or sweeps during turning by motor 32). Cable 80 in a particular example has a first channel or conductor 82 to power transducer 28, and a second channel or conductor 84 to conduct signals generated by reception of ultrasound signals by element 42 to imaging system 34. Cable 80 also serves as a linear marker that attenuates the ultrasound beam (for example by reflection) to a greater degree than wall 24 attenuates the ultrasound beam. The greater attenuation of cable 80 amidst the much smaller attenuation (e.g. through reflection, refraction, scattering or absorption) of wall 24 presents a varied attenuation condition for wall 24, in which ultrasound (emitted beam or reflected echoes) relatively easily moves through or across wall 24 except where cable 80 lies. Thus, an ultrasound signal produced at the discrete location of cable 80 within window or field 36 is substantially different from those produced at other locations within field 36, which results in a substantially different RF signal produced by transducer 28 for sending to a viewer. For example, the RF signal relating to the discrete location of cable 80 may have a much larger amplitude, indicating substantial reflection from that location, than is otherwise produced by transducer 28 relative to other locations on wall 24. As another example, the RF signal relating to that discrete location may have a much smaller amplitude (or close to zero) than other signals, indicating blockage of ultrasound approaching transducer 28 by cable 80. In some embodiments, the reflection, blockage or other attenuation due to cable 80 may extend to an angle B (see FIG. 3), which may be about 15 degrees of arc in ultrasound field 36 (1/24 of the image area).

In the illustrated embodiment, cable 80 is parallel to the longitudinal axis A of device 20 through the entirety of ultrasound field 36. As the ultrasound beam proceeds around the circumference of wall 24, it will be attenuated substantially uniformly by wall 24—for instance, wall 24 will pass all or a substantially uniform fraction of the ultrasound energy in the beam. When the ultrasound beam encounters cable 80, cable 80 blocks some or all of the beam directed at it. The reflected ultrasound at that discrete location (e.g. region B in FIG. 3) will produce an RF signal (representing echo(es) received by transducer 28) markedly different from the regions of the ultrasound field without cable 80. For example, the RF signal produced from emissions directed toward or received from the direction of cable 80 may be substantially more powerful (e.g. a greater intensity) than that received at other locations along wall 24, indicative of essentially entire reflection of the ultrasound beam by cable 80. As another example, the RF signal may be or approach zero because cable 80 scatters the ultrasound beam, and no return ultrasound echo can approach transducer 28 through cable 80. When the distinctive signal is encountered by imaging system 34 (e.g. viewing software and apparatus), imaging system 34 observes that distinctive signal and determines that the beam is pointed toward cable 80. Accordingly, the position of the ultrasound beam with respect to cable 80 on wall 24, other static portions of device 20, and/or tissue or marker within the body is known with precision. Image frames (e.g. successive frames) are registered by imaging system 34 using the distinctive signal characteristic provided by cable 80 as a marker or indicator of the static position of cable 80, so that successive images are displayed in the same position and/or orientation for viewing by the physician or other operator.

Cable 80 is shown in this embodiment to be inside chamber 26, on an interior surface of wall 24. It will be understood that cable 80 could be arranged on the outside of device 20 along wall 24, but an arrangement in which cable 80 is within chamber 26 does not increase the outside diameter of device 20 or provide it with an irregular outer surface, which may be disadvantageous in the realm of intravascular usage. In other embodiments, cable 80 is placed within wall 24, i.e. between its inner and outer diameters among the matter of wall 24. For example, cable 80 may be placed in forming wall 24 initially, or between layers of material in wall 24. Such an arrangement does not enlarge or present an odd outer configuration, and maintains a maximum of space within chamber 26 for the operating components. Further, if cable 80 is not needed for transfer of electrical signals to or from transducer 28, a metallic strip or layer may be placed in wall 24 or on a surface thereof to provide the attenuation noted above. Such a strip or layer provides an even lower profile for the device.

Figure 3:
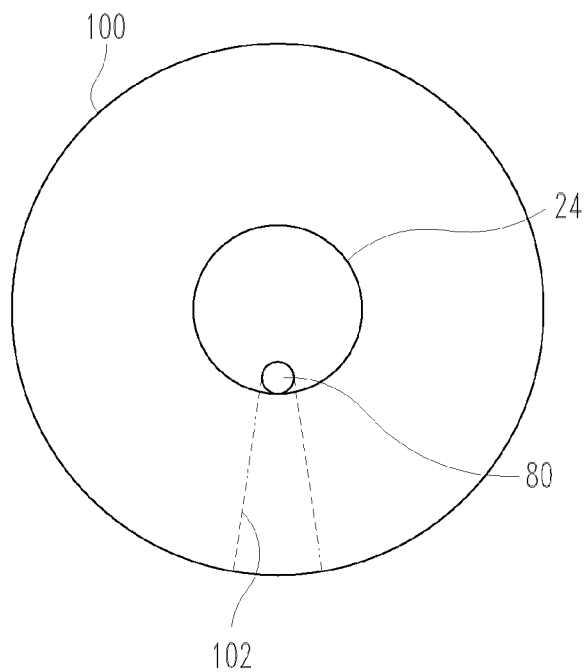
FIG. 3 is a schematic representation of an embodiment of an ultrasound field produced by the embodiment of FIG. 1, viewed on and along a longitudinal axis.

It will be appreciated that a variety of materials or features that create the varied-attenuation wall 24, as by partially or fully blocking ultrasound to an extent different than any blockage provided by the rest of wall 24, can be used as an encoder or registration tool. For example, in the embodiment shown in FIG. 2, two sections 90, 92 of a thin metal film, coating or layer are placed on wall 24. The particular embodiment shown has sections 90, 92 on the interior of wall 24 (i.e. facing or adjoining chamber 26), although it will be understood that such sections 90, 92 may be placed on the outside of wall 24 or within wall 24, i.e. between its inner and outer diameters. In the embodiment of FIG. 3, the film is deposited on the inside of wall 24 using techniques such as sputtering or electro-plating, and in other embodiments may be placed outside (on the outer surface of) wall 24. In particular embodiments, only one side of the ultrasound window (e.g. the inside or the outside) is coated with the thin film to minimize acoustic attenuation. The illustrated embodiment shows two sections 90, 92 separated by two open or uncovered portions 94, 96. Portions 94, 96 are diametrically opposed to each other and subtend substantially the same arc in this embodiment. It will be understood that a single open portion or more than two such open portions may be provided.

It will be understood that a number of substances providing a difference in ultrasound attenuation may be used for a film or layer in sections 90, 92. Metals (e.g. aluminum) have been used for electrical conductivity, and particular embodiments of a thin conductive layer for sections 90, 92 of gold, platinum, or rhodium may be used for their biocompatibility, high conductivity and resistance to oxidation. Using efficient conductors of electricity for the film in sections 90, 92 permits use of those sections 90, 92 to conduct electrical signals through the ultrasound field as well as providing a difference in ultrasound attenuation in field 36 in the varied-attenuation wall 24 of device 20. Such a thin conductive film has high electrical conductivity as well as allowing acoustic transmission, allowing an ultrasound window having such a film to conduct signals across or through the window (i.e. along the longitudinal axis) while obtaining a viewable image behind the conductor. In particular embodiments, the layers or coatings are between about 0.1 μm and 20 μm in thickness, such as approximately 2 μm thick. The sections cover more than half of the ultrasound window in certain embodiments, and a particular example (e.g. FIG. 4) each section 90, 92 covers about 150 degrees of the window, with uncoated areas between them each covering about 30 degrees and diametrically opposed to each other. In other embodiments, the respective arcs subtended by sections 90, 92 may be up to about 160, up to about 170 or up to about 175 degrees. It will also be understood that in other embodiments the arcuate extent of sections 90, 92 (and/or the spaces between them) may be unequal.

Such thicknesses have been tested and found to operate as desired. Thicker layers may be usable, but will increase acoustic reflection (and therefore a reduction in the acoustic energy passed through wall 24 in both exit and return) and reduce loss of electrical signal, and vice-versa. Both such losses degrade image quality and should accordingly be minimized. Acoustic reflectivity (and therefore acoustic loss in the device 20) is related to the impedance mismatch between the film and the surrounding materials (e.g. water or blood), film thickness, and ultrasonic wave frequency. From testing, it has been found that a 16 µm thick aluminum film results in an acoustic loss of less than 4 dB in a round trip, i.e. a pulse echo from transducer 28 outward and back, twice through the film(s) on ultrasound window. It is expected that a thin gold film will cause less than 5 dB of ultrasound attenuation during such a round trip.

Embodiments using a thin metallic layer or coating as noted above provide the advantage of imaging in a complete 360 degree area, while still permitting registration of images. As seen schematically in FIGS. 3-4, embodiments using a cable or other elongated side ultrasound-reflective (e.g. having a high acoustic impedance) piece are compared to those using a thin film as acoustic attenuator. In FIG. 3, the ultrasound beam turns around an axis perpendicular to (out of) the page, with cable 80 statically placed to one side on wall 24. Outer circle 100 represents an area (e.g. tissue such as a blood vessel) to be imaged, showing an interior in which the ultrasound beam travels. As the beam turns, each revolution passes cable 80, which generates an unvisualizable or less-visualizable wedge area 102 behind cable 80. As indicated above, that area 102 may be an area of about 15 degrees of arc or less. The remainder of the tissue or area is easily imaged, and the wedge area 102 remains static and is used to register images with one another, as discussed above.

Figure 4:
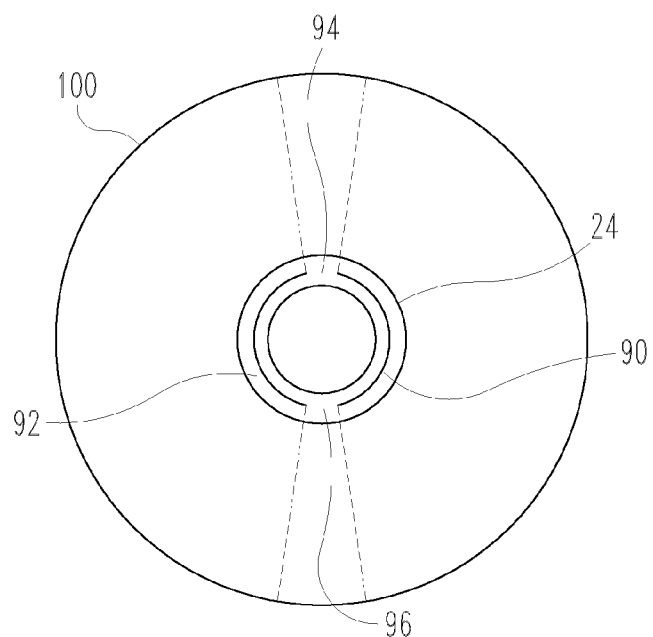
FIG. 4 is a schematic representation of an embodiment of an ultrasound field produced by the embodiment of FIG. 2, viewed on and along a longitudinal axis.

In FIG. 4, the beam likewise turns around an axis out of the page, and has two sections 90, 92 of thin metallic layer along wall 24. The layer, as discussed previously, allows acoustic transmission but to a lesser degree than the open spaces 94, 96 between sections 90, 92. Again, outer circle 100 in FIG. 4 represents area (e.g. a vessel portion) to be imaged. As the beam turns, it passes through sections 90, 92 with some attenuation, but with sufficient acoustic energy moving through sections 90, 92 to image the desired area. Open spaces 94, 96 provide a stronger acoustic signal return to transducer 28, which is used for registration of images. The coated or layered sections 90, 92 reduce the image quality slightly and limits the total imaging depth over a larger arc, but allow imaging over the whole ultrasound field or window 36, while the cable 80 prevents or limits visualization in an angle behind it but does not affect visualization in other parts of the field or window 36.

In the example in which two sections 90, 92 are coated with the thin layer, with an uncoated area separating the sections, the sections can have separate electrical functions. For example, one section 90 can carry electronic (RF) signals to and from transducer 28, to power transducer 28 to emit an ultrasound beam and to carry the signal from transducer 28 representing the reflection of the ultrasound beam, for generating the image of the tissue. The other section 92 can function as a ground. Thus, the uncoated areas 94, 96 function both for registration of the images, since they allow through a different strength of signal from that allowed through sections 90, 92, and for the electrical insulation of the sections 90, 92 from each other.

It will also be understood that thin films or layers of metallic or other conductive materials may be used as conductors for transducer 28 or for other uses in other ways. Referring generally to FIG. 5, there is shown an embodiment of an internal ultrasound device 120 having a flexible elongated member 22 (e.g. a catheter or other tubular member) with a wall 24 defining an internal chamber 26, with catheter 22 being sized and configured for insertion into and/or travel along the vascular system. Within chamber 26 is a transducer 28, which in this embodiment is for emitting an ultrasound beam and for receiving reflected ultrasound and sending electronic signals representing the reflected ultrasound. A window or field 36 for the ultrasound beam is indicated. Member 22, wall 24, chamber 26, transducer 28 and window 36 are all similar or identical to embodiments described above.

Wall 24 includes an inner surface 131 generally facing transducer 28 (e.g. inward toward the longitudinal axis of device 120) and an outer surface 133 generally facing away from transducer 28. Inner surface 131 will thus generally define at least a portion of chamber 26. On at least a portion of inner surface 131, there is a film or thin layer 190 of metallic material, as for example one or more of the materials noted above with respect to sections 90, 92. In the illustrated embodiment, film 190 extends all the way around the perimeter (in this case, a circumference) of inner surface 131, and is within a part of window 36. In other embodiments, film 190 may extend less than all the way around the perimeter. Further, other embodiments may include a film 190 having a length along the longitudinal axis of device 120 that encompasses all of window 36, or that is not within window 36 at all. Similarly, at least a portion of outer surface 133 includes a film or thin layer 192 of metallic material. In the illustrated embodiment, film 192 extends all the way around the perimeter (in this case, a circumference) of outer surface 133, and is within a part of window 36. In other embodiments, film 192 may extend less than all the way around the perimeter. Further, other embodiments may include a film 192 having a length along the longitudinal axis of device 120 that encompasses all of window 36, or that is not within window 36 at all. The illustrated embodiment shows films 190, 192 overlapping each other, i.e. a diameter of device 20 intersects each film 190, 192, while they are separated by wall 24. It will be understood that other embodiments may have first and second films or coatings (e.g. films 190, 192) on the same surface (e.g. one of surfaces 131 and 133) that do not overlap. For example, two coatings 190, 192 can be placed, electrically insulated from each other (e.g. by a non-conductive space), on separate halves, opposed areas, on the same side of window 36 (e.g. each or both covering a part of the perimeter of window 36), or other sections of the inner surface 131 or of the outer surface 133, thus having the coatings on the same surface but electrically isolated from one another.

Figure 6:
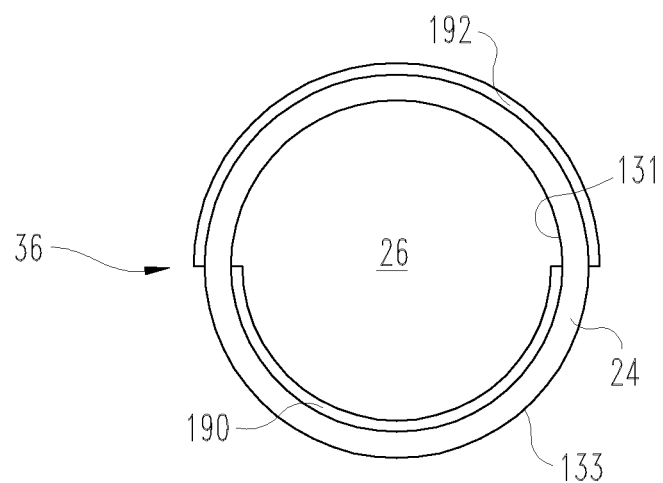
FIG. 6 is a schematic representation of an embodiment of a portion of an internal ultrasound device as further disclosed herein.

Another embodiment of placement of films 190, 192 is shown schematically in FIG. 6, in which film 190 is on an inner surface 131 in one area of window 36, and film 192 is on an outer surface 133 in another area of window 36. The illustration shows that films 190 and 192 extend about separate arcs of about 180 degrees, so that they do not overlap. It will be understood that films 190, 192 may each cover a smaller arc, may each cover different arcs from each other, and may be opposite each other or otherwise placed. Such an embodiment provides an effect on an ultrasound beam that is different in the area covered by film 190 compared to that covered by film 192, at least because of the differing travel distance for the ultrasound beam to move from a transducer or reflector to the respective films 190, 192. Thus, the ultrasound beam that travels along a path intersecting film 192 travels a longer distance (and takes a longer time) before encountering film 192 compared to the distance and time for the ultrasound beam that travels along a path intersecting film 190. Other effects on the ultrasound beam by films 190, 192 or other pieces (as noted herein) may also be present.

Films 190, 192 form separate electronic conductors that are insulated from each other, as by the material of wall 24 in the illustrated embodiment. Each of films 190, 192 are separately electronically connected to transducer 28 in this embodiment, so that one film acts as a signal conductor and the other as a ground. In the example of FIG. 5, the outer film 192 is the ground, and inner film 190 is the signal conductor. Films 190, 192 may be of the same materials and prepared in substantially the same or identical ways as sections 90, 92 noted above. When of a thickness as noted above, films 190, 192 permit ultrasound imaging through them, even though there may be attenuation (as by reflection, refraction or absorption). It will be understood that films 190, 192 as conductors may be used with or without the feedback or registration characteristics discussed above with respect to sections 90, 92. For example, in embodiments in which both films 190, 192 extend around their respective perimeters and extend along most or all of window 36, the attenuation due to films 190, 192 will be substantially constant within window 36, so that electronic signals sent by the transducer will not have an amplitude or other difference that permit registration or alignment of signals or images.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected. Examples of other features or embodiments useful in connection with the particular embodiments discussed above are found in the application filed on Oct. 12, 2012, entitled "Mechanical Scanning Ultrasound Transducer with Micromotor" (Application Ser. No. 61/713,186), which is incorporated herein in its entirety. It will be understood that features or attributes noted with respect to one or more specific embodiments may be used or incorporated into other embodiments of the structures and methods disclosed.

What is claimed is:

1. An internal ultrasound device with a feedback system, comprising:
   a transducer for emitting and/or receiving an ultrasound beam, the beam adapted to rotate around at least a portion of the device;
   an ultrasound-transparent wall through which at least part of the ultrasound beam passes, the wall having an external diameter, the wall having two first portions of the wall separated by a second portion of the wall, each first portion of the wall with a thin metal film entirely inside the external diameter, the thin metal films having electrical conductivity and allowing passage of an ultrasound beam,
      wherein the thin metal film of a first of the two first portions of the wall is electrically connected to the transducer to carry signals to and from the transducer, and the thin metal film of a second of the two first portions is grounded, and
      wherein the ultrasound beam, as it rotates, at least periodically travels along a first path that intersects any of the two first portions of the wall and the transducer so that the ultrasound beam passes through the thin metal film with some attenuation and a second path that intersects the second portion of the wall and the transducer, so that a first electronic signal generated by the transducer representing received ultrasound along the first path has at least one signal characteristic different from a second electronic signal generated by the transducer representing received ultrasound along the second path; and
   an ultrasound control system adapted to:
      receive and assess a plurality of electronic signals from the transducer representing received ultrasound along a path of the ultrasound beam as the ultrasound beam rotates,
      detect the at least one signal characteristic difference amongst the plurality of electronic signals, and
      register the plurality of the electronic signals with each other by reference to the detected at least one signal characteristic difference.

2. The device of claim 1, wherein the first portion of the wall is configured to attenuate the ultrasound beam to a first degree and the second portion of the wall is configured to attenuate the ultrasound beam to a second degree.

3. The device of claim 1, wherein the second portion of the wall does not include a thin metal film, so that the ultrasound attenuation due to interaction with the first portions of the wall is different from ultrasound attenuation due to interaction with the second portion of the wall.

4. The device of claim 1, comprising two of the second portions, the second portions being positioned at diametrically opposed locations.

5. The device of claim 1, wherein the thin metal film comprises at least one of gold, platinum, rhodium, silver, copper and aluminum.

6. The device of claim 1, wherein the thickness of the thin metal film is approximately 1 μm to 20 μm.

7. The device of claim 1, wherein the transducer is configured to:
   emit the ultrasound beam, and
   rotate in at least a 360 degree arc to turn the beam.

8. The device of claim 1, wherein the transducer is configured to emit and receive the ultrasound beam, the device further comprising a mirror configured to turn in at least a 360 degree path to reflect the emitted ultrasound beam from the transducer and reflect the received ultrasound beam to the transducer.

9. The device of claim 1, wherein the two first portions of the wall each subtend an arc along the wall, the arc's central angle within the range of 150 degrees to 175 degrees.

10. The device of claim 1, wherein the wall has an inner surface facing the transducer and defining an inner diameter, and the thin metal film is disposed on the inner surface.

11. The device of claim 1, wherein the wall has an inner surface facing the transducer and defining an inner diameter, and wherein the thin metal film is disposed in the wall, between the inner diameter and the outer diameter.

12. The device of claim 1, wherein an ultrasound beam from the transducer that passes outward through the thin metal film and returns as an echo through the thin metal film to the transducer experiences an acoustic loss, due to interaction with the thin metal film, of less than 5 dB and greater than 0 dB.

13. An internal ultrasound device with a feedback system comprising:
- a transducer for emitting and/or receiving an ultrasound beam, the beam adapted to rotate around at least a portion of the device;
- an ultrasound-transparent wall through which at least part of the ultrasound beam passes, the wall having an external diameter, the wall having a first portion of the wall with a first thin metal film disposed thereon and a second portion of the wall with a second thin metal film disposed thereon, the thin metal films having electrical conductivity and allowing passage of an ultrasound beam,
    - wherein the first thin metal film is electrically connected to the transducer to carry signals to and from the transducer, and the second thin metal film is grounded,
    - wherein the ultrasound beam, as it rotates, at least periodically travels along a first path that intersects the first portion of the wall and the transducer so that the ultrasound beam passes through the first thin metal film with some interaction therebetween and a second path that intersects the second portion of the wall and the transducer so that the ultrasound beam passes through the second thin metal film with some interaction therebetween, and
    - wherein the first and second thin metal films are located so that the ultrasound beam must travel further before interacting with the first thin metal film than the ultrasound beam must travel before interacting with the second thin metal film, so that at least one first signal characteristic of a first electronic signal generated by the transducer representing interaction between the first thin metal film and received ultrasound along the first path is delayed relative to at least one second signal characteristic of a second electronic signal generated by the transducer representing interaction between the second thin metal film and received ultrasound along the second path; and
- an ultrasound control system adapted to:
    - receive and assess a plurality of electronic signals from the transducer representing received ultrasound along a path of the ultrasound beam as the ultrasound beam rotates,
    - detect, from amongst the plurality of electronic signals, the at least one first characteristic, the at least one second characteristic, and the relative delay therebetween, and
    - register the plurality of the electronic signals with each other by reference to the detected delay.

* * * * *